United States Patent [19]

Dalton

[11] 4,174,443
[45] Nov. 13, 1979

[54] AZA-BIS-LACTAMS

[75] Inventor: Philip B. Dalton, Brookville, N.Y.

[73] Assignee: GAF Corporation, New York, N.Y.

[21] Appl. No.: 865,857

[22] Filed: Dec. 30, 1977

[51] Int. Cl.$^2$ .................. C07D 241/08; C07D 265/32; C07D 207/26

[52] U.S. Cl. ...................... 544/86; 544/130; 544/137; 544/139; 544/141; 544/357; 544/365; 544/369; 544/370; 260/239.3 R; 71/88; 71/92; 424/248.56; 424/250; 548/318; 546/188; 546/209; 546/210; 544/372; 260/243.3; 260/244.4; 260/307 C; 260/245.5; 260/245.6; 260/326.25; 548/228

[58] Field of Search ............ 260/326.25; 544/357, 86

[56] References Cited

U.S. PATENT DOCUMENTS 3,156,687  11/1964  Andersen et al. ...................... 544/86
3,660,388  5/1972   Dazzi ..................................... 544/86

*Primary Examiner*—Jose Tovar
*Attorney, Agent, or Firm*—Walter C. Kehm

[57] ABSTRACT

Novel aza-bis-lactams having the formula:

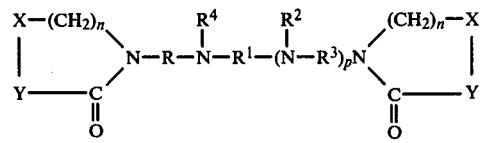

wherein n is an integer from 1 to 3; p is 0 or 1; $R^2$ and $R^4$ are independently hydrogen, alkyl having from 1 to 4 carbon atoms, or phenyl; X is methylene, an oxygen atom or $-N<R^2$; Y is methylene or, when X is methylene, then Y can also be $-N<R^2$; and R, $R^1$ and $R^3$ are independently alkylene having from 2 to 6 carbon atoms.

17 Claims, No Drawings

AZA-BIS-LACTAMS

The present invention relates to new and useful aza and diaza-bis-lactams and a method for their preparation.

The compounds of the present invention are useful as intermediates for surfactants, ion exchange resins, antidusting agents, solvents and saponification agents for acids. They also find utility as detergents, chemosterilants, fungicides, insecticides and herbicides.

Unlike the acyclic polyethylene polyamines, heretofore employed in similar applications, the present compounds are substantially noncorrosive so that they may be handled and shipped without undue precaution. The compounds of this invention are also nonirridating to the eyes and skin tissue so that they may find cosmetic application as skin conditioners and antiseptic lotions.

It is an object of the present invention to provide new and useful non-corrosive, non-irridating compounds.

Another object of this invention is to provide an economical and commercially feasible method for the preparation of the present compounds.

Still another object of the invention is to provide useful chemical intermediates having several reactive sites for the formation of other useful chemical products.

These and other objects will become apparent from the accompanying description and disclosure.

According to this invention there is provided an aza- or diaza-bis-lactam having the formula:

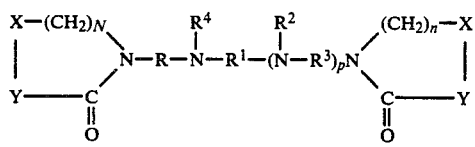

wherein n is an integer from 1 to 3; p is 0 or 1; $R^2$ and $R^4$ are independently hydrogen, alkyl having from 1 to 4 carbon atoms or phenyl; X is methylene, an oxygen atom or $-N<R^2$; Y is methylene or, when X is methylene, then Y can also be $-N<R^2$; and R, $R^1$ and $R^3$ are independently alkylene having from 2 to 6 carbon atoms.

The compounds of the present invention are produced by reacting an aza-alkyl diamine having the formula:

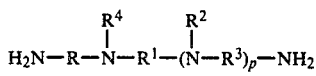

wherein p, R, $R^1$, $R^2$, $R^3$ and $R^4$ are as defined above in formula I, with an O-heterocyclic carbonyl compound containing within the ring structure the group

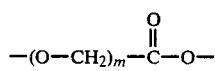

or the group

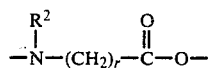

where m and r are 0 or 1, and $R^2$ is as defined above in Formula I. Such O-heterocyclic carbonyl compounds are illustrated by the formula:

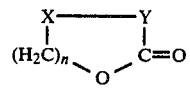

wherein n, X and Y are as defined in Formula I. The preferred O-heterocyclic carbonyl reactants of this invention are those wherein n is 1 to 3, and X and Y are methylene.

Specific examples of the O-heterocyclic carbonyl reactants are butyrolactone, caprolactone, p-dioxanone, N-methyl-2-morpholone, 2-oxazalone and lower alkyl ($C_1$–$C_4$) substituents thereof. Of this group, the butyrolactone is the most preferred.

Specific examples of the aza-alkyl diamine reactant include 3-azahexane-1,6-diamine; 4,7-diazadecane-1,10-diamine; N-methylimino-bis-(propylamine); 3-azaheptane-1-7-diamine; 5-azadecane-1,11-diamine; 4,9-diazadodecane-1,12-diamine; imino-bis-(butylamine); N-methylimino-bis-(hexylamine), N-phenylimino-bis-(propylamine) etc. Of these, the most preferred are those wherein R and $R^1$ and $R^3$ are alkylene having from 2 to 3 carbon atoms and, when p is 1, $R^2$ and $R^4$ are hydrogen or methyl. The azaalkyl diamine reactants of this invention are known and are commercially available, (e.g. supplied by BASF Aktiengesellschaft and by Jefferson Chemical, a division of Texaco, Inc.).

The reaction to produce the products of the present invention can be carried out over a period of from about 2 to 15 hours at a temperature of between about 180° C. and about 325° C., under a pressure of from about 50 psig. to about 400 psig. However, preferred reaction conditions include a reaction time of from about 4 to about 10 hours, at a temperature of from about 225° C. to about 275° C. under from about 225 psig to about 325 psig. The present reaction is conveniently carried out in an autoclave with agitation which may be supplied by a mechanical stirrer, a vibrator, or any other conventional means of mixing or agitating device. The reactants may enter the reaction zone in admixture or may be introduced separately thereto in any order of addition. Alternatively, a portion of either or both reactants may be pressurized into the reactor in incremental amounts during reaction. Preferably when intermittent addition of either reactant is employed, introduction of all reactants is completed within a period of less than 2 hours.

The mole ratio of aza-alkyl diamine to O-heterocyclic carbonyl compound introduced into the reaction zone is between about 1:1.75 and 1:10; preferably, between about 1:2 and about 1:3 or as close as stoichiometry as is convenient. Since the product of the reaction is generally obtained as a high molecular weight liquid or oil, it is easily separated from any unreacted components after the reaction has been allowed to proceed for several hours. Accordingly, when an amount of either reactant in excess of that required for reaction on a mole to 2 mole basis is employed, unreacted components may be easily separated and recycled to reactor so that the conversion can be carried out to extinction of unreacted species.

Whether or not recycle or unreacted components is contemplated, the product mixture after leaving the reactor is generally cooled and stripped of volatiles, i.e.

mainly water, at a pot temperature of between about 100 and about 200° C. under subatmospheric pressure, preferably at a pot temperature of between about 140° C. and about 160° C. under from about 0.2 to about 1 mm Hg. In the absence of recycle, conversions between 70 and 90% are obtainable. Further purification of the product can be effected, if desired, by vacuum distillation, for example under a vacuum of from 0.05 to about 0.5 mm Hg.

The reaction of the present invention, with the formation of a diol intermediate, may be illustrated as shown below. The letters designated in the following equation are defined as above in Formulae I through III.

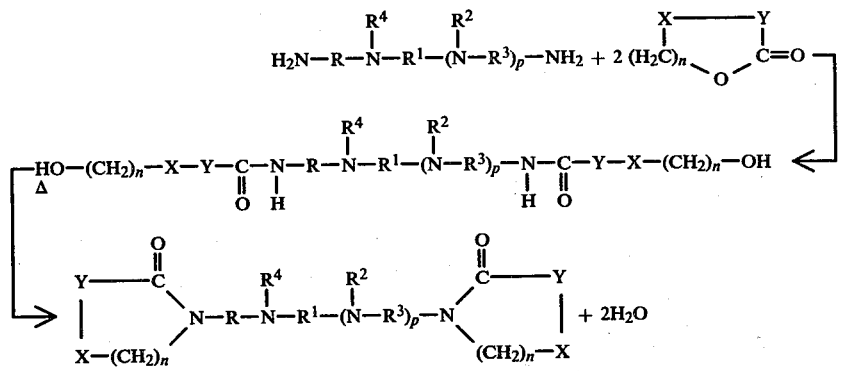

The above reaction can employ an inert liquid solvent, up to about 50 weight % concentration, for better distribution of the reactant species, if desired. However, the use of a solvent is not required to achieve resonable conversion to substantially pure product. Reference is now had to the following Examples which illustrate specific and preferred embodiments of the present invention. All amounts and proportions referred to therein are by weight unless otherwise indicated. It will be understood that the scope of this invention is not limited to the accompanying examples and that other species of reactants set forth hereinabove can be substituted in the following examples to provide the novel products of this invention having the utility set forth above.

EXAMPLE 1

PREPARATION OF 3-AZAHEXANE-1,6-(2-PYRROLIDONE)

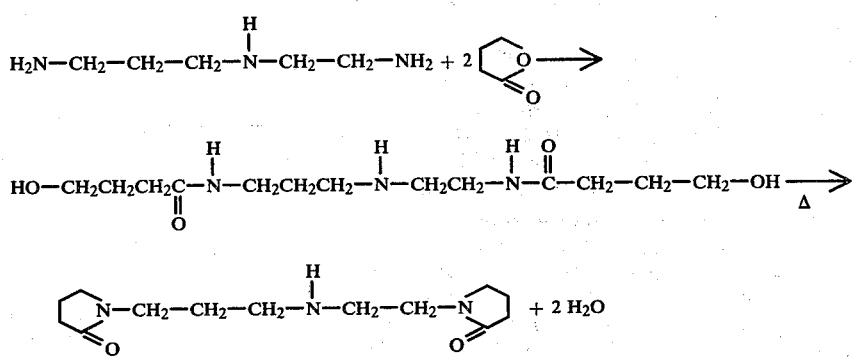

A one liter stainless steel stirred autoclave was purged with $N_2$, evacuated and then charged with 117 g (1 mole) 3-azahexane-1,6-diamine together with 172 g (2 moles) butyrolactone. The autoclave was sealed and heated to 250° C. over 1–2 hours and maintained at 250° C. under 260 psig for 6 hours.

After 6 hours the autoclave was cooled to room temperature and the reaction mixture (289 g) was discharged.

The reaction mixture was stripped of volatiles (water) at a pot temperature of 150° C. under 0.5 mm Hg to provide 259 g of crude 3-azahexane-1,6-(2-pyrrolidone).

Infra red, nuclear magnetic resonance and high pressure liquid chromatography analysis indicated the purity of the product was about 80%.

A 50 g portion of the crude product was further purified by vacuum distillation at 180° C. under 0.1 mm Hg to provide 33 g of pure 3-azahexane-1,6-(2-pyrrolidone), recovered as a light yellow liquid.

EXAMPLE 2

PREPARATION OF 4,7-DIAZADECANE-1,10-(2-PYRROLIDONE)

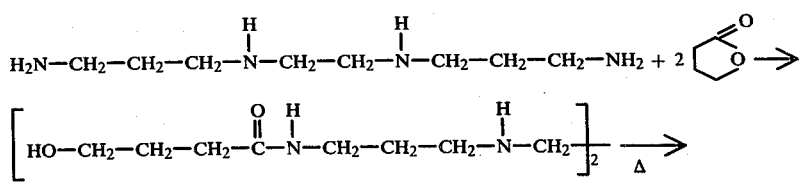

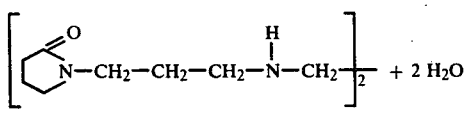

A one liter stainless steel stirred autoclave was purged with N₂, evacuated and then charged with 174 g (1 mole) of 4,7-diazadecane-1,10-diamine and 172 g (2 moles) of butyrolactone. The autoclave was sealed and heated to 250° C. over 1-2 hours and maintained at 250° C. under 300 psig for 6 hours.

After 6 hours the autoclave was cooled to room temperature and the reaction mixture (346 g) was discharged.

The reaction mixture was stripped of volatiles (water) to a pot temperature of 150° C. under 0.5 mm Hg to provide 308 g of crude 4,7-diazadecane-1,10-(2-pyrrolidone) recovered as an amber colored liquid.

Infra red and nuclear magnetic resonance analysis indicated a product purity of about 70%.

EXAMPLE 3

PREPARATION OF METHYLIMINO-BIS-PROPYL-3-(2-PYRROLIDONE)

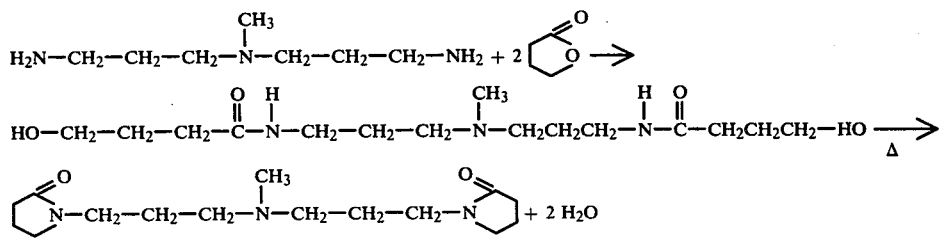

A one liter stainless steel stirred autoclave was purged with N₂, evacuated and then charged with 145 g (1 mole) N-methylimino-bis-(propylamine) and 172 g (2 moles) of butyrolactone. The autoclave was sealed and heated to 250° C. over 1-2 hours and maintained at 250° C. under 308 psig for 6 hours.

After 6 hours the autoclave was cooled to room temperature and the reaction mixture (317 g) was discharged.

The reaction mixture was stripped of volatiles (water) to a pot temperature of 150° C. under 0.5 mm Hg to provide 265 g of crude product.

Infrared and nuclear magnetic resonance analysis indicated a product purity of 95+%.

The crude product was distilled in vacuo at 190°-200° C. under 0.2 mm Hg to provide 203 g of pure methyliminobis-propyl-3-(2-pyrrolidone), recovered as a yellow liquid.

EXAMPLE 4

PREPARATION OF 3-AXAHEXANE-1,6-(3-MORPHOLONE)

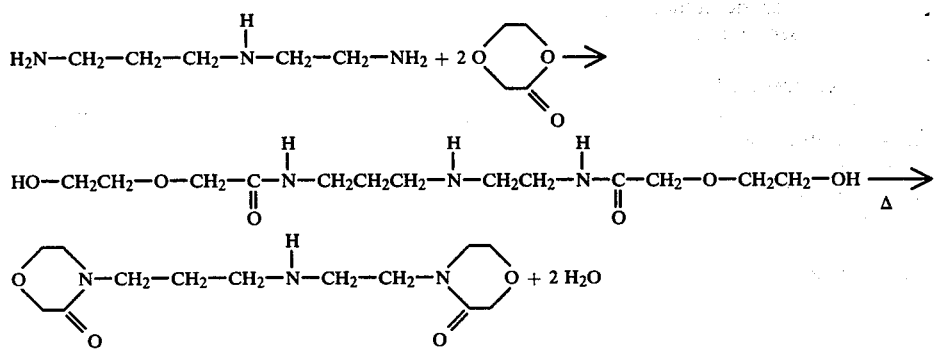

To a purged one liter stainless steel stirred autoclave is added 117 g (1 mole) 3-azahexane-1,6-diamine and 250 g (2 moles) p-dioxanone. The autoclave is sealed and heated to 250° C. over 1-2 hours and then maintained at 270° C. under 260 psig for 8 hours, after which the autoclave is cooled and the reaction mixture (337 g) is discharged from the reactor.

The reaction mixture is stripped of volatiles (water) to a pot temperature of 150° C. under 0.5 mm Hg giving about 25 g of crude liquid 3-azahexane-1,6-(3-morpholone) or about 70% conversion to product.

EXAMPLE 5

PREPARATION OF 4,7-DIAZADECANE-1,10-(N-METHYL-2-PIPERAZONE)

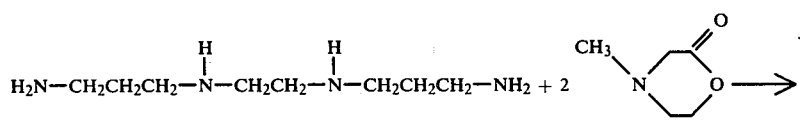

-continued

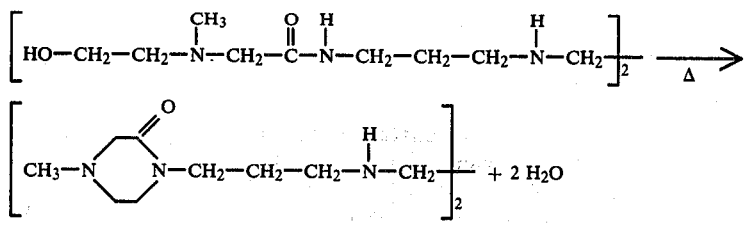

To a purged one liter stainless steel stirred autoclave is added 175 g (1 mole) 4,7-diazadecane-1,10-diamine and 235 g (2 moles) N-methyl-2-morpholone and then sealed. The reaction is heated to 250° C. over 1–2 hours and maintained at 280° C. under 350 psig for 6 hours after which the autoclave is cooled and the reaction mixture (410 g) is discharged from the reactor.

The reaction mixture is stripped of volatiles (water) to a pot temperature of 150° C. under 0.5 mm Hg giving about 30 g of crude liquid 4,7-diazadecane-1,10-(N-methyl-2-piperazone) or about 70% conversion to product.

The above-prepared products can be employed in their crude state as removed from the reactor and containing volatiles when they are used as a component in a high energy fuel. However, when used as a chemical intermediate, softening agent, or ion exchange resin, it is usually desirable to purify the product as set forth above and to disperse it in a suitable carrier, e.g. cyclohexane, benzene, xylene, toluene, or a $C_1$ to $C_6$ aliphatic alcohol, wherein the concentration of the present aza- or diaza-bislactams are maintained in a concentration of between about 0.05 and about 25 wt % (preferably between about 1 and about 12 weight %). When the products of the present invention are to be employed as fungicides, herbicides, insecticides or chemosterilants, their concentration in a suitable carrier need not exceed 100,000 ppm, and is preferably employed at a concentration of between about 10 and about 500 ppm. In this application, the product or a mixture of products of the present invention can be dispersed or dissolved in a suitable liquid carrier such as an aliphatic alcohol, acetone, ethyl ether, methyl ethyl ketone, cyclohexane, benzene, toluene, xylene, etc. or any other conventional, inert liquid carrier. The product of the present invention can also be applied as a granular dust or powder by absorbing the chemical or the mixture of chemicals on a solid carrier such as talc, diatomaceous earth, bentonite, or any of the other conventional and inert solid carriers. The chemical composition is then applied to plants at a rate of between about 3 to about 25 grams per acre. The products of the present invention are particularly useful in the control of powdery mildew fungus on plants.

When employed as a skin conditioner, the present compounds are usually applied as a cream or liquid in a concentration of about 0.005 and about 10 ppm in an inert cosmetically acceptable carrier such as lanolin, facial cleansing cream, glycerin, or any of the other conventional cosmetic lotions or creams. The resulting compositions are particularly effective in the control of acne and minor skin blemishes.

I claim:

1. An aza-bis-lactam having the formula:

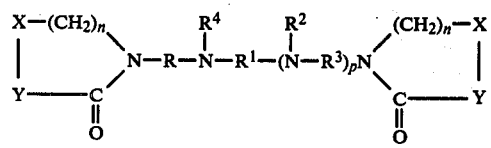

wherein n is an integer from 1 to 3; p is 0 or 1; $R^2$ and $R^4$ are independently hydrogen, alkyl having from 1 to 4 carbon atoms or phenyl; X is methylene, an oxygen atom or $-N<R^2$; Y is methylene or, when X is methylene, then Y can also be $-N<R^2$; and R, $R^1$ and $R^3$ are independently alkylene having from 2 to 6 carbon atoms.

2. The compounds of claim 1 wherein X and Y are methylene.

3. The compound having the formula:

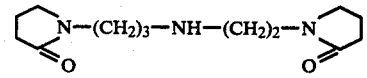

4. The compound having the formula:

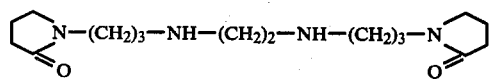

5. The compound having the formula:

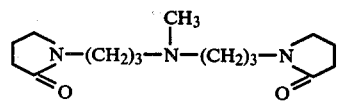

6. The compound having the formula:

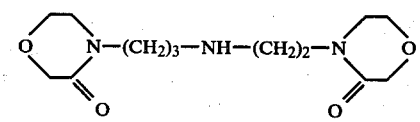

7. The compound having the formula:

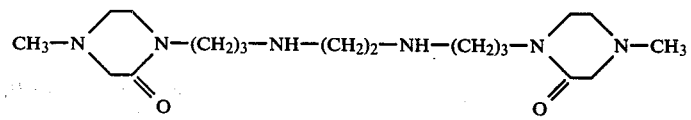

8. The process for the preparation of compounds of claim 1 which comprises contacting an azaalkyldiamine having the formula:

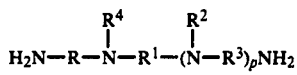

wherein p is 0 or 1; $R^2$ and $R^4$ are independently hydrogen, alkyl having from 1 to 4 carbon atoms or phenyl; and R, $R^1$ and $R^3$ are alkylene having from 2 to 6 carbon atoms, with an O-heterocyclic carbonyl compound having the formula:

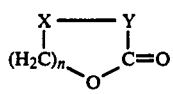

wherein n, X and Y are as defined in claim 1, at a temperature of between about 180° C. and about 325° C. under between about 50 psig and about 400 psig for a period of from about 2 to about 15 hours.

9. The process of claim 8 wherein the reaction is carried out at from about 220° C. to about 275° C. under from about 225 psig to about 325 psig for a period of between about 4 and about 10 hours while agitating the mixture.

10. The process of claim 8 wherein the azaalkyldiamine is 3-azahexane-1,6-diamine.

11. The proces of claim 8 wherein the azaalkyldiamine is 4,7-diazadecane-1,10-diamine.

12. The process of claim 8 wherein the azaalkyldiamine is methylimino-bis-(propylamine).

13. The process of claim 8 wherein the O-heterocyclic carbonyl compound is butyrolactone.

14. The process of claim 8 wherein the O-heterocyclic carbonyl compound is p-dioxanone.

15. The process of claim 8 wherein the O-heterocyclic carbonyl compound is N-methyl-2-morpholone.

16. The process of claim 8 wherein the mole ratio of azaalkyldiamine to O-heterocyclic carbonyl compound is between about 1:1.75 and about 1:10.

17. The process of claim 16 wherein said mole ratio is between about 1:2 and about 1.3.

* * * * *